United States Patent [19]

Kodaira et al.

[11] 4,305,889
[45] Dec. 15, 1981

[54] PROCESS FOR PRODUCING α, α, α-TRIFLUORO-O-TOLUIC FLUORIDE

[75] Inventors: Tsumoru Kodaira, Takatsuki; Kunihiro Yabutani, Neyagawa; Hitoshi Kurono, Toyonaka, all of Japan

[73] Assignee: Nihon Nohyaku Co., Ltd., Tokyo, Japan

[21] Appl. No.: 128,184

[22] Filed: Mar. 7, 1980

[30] Foreign Application Priority Data

Mar. 17, 1979 [JP] Japan ................................. 54-31300

[51] Int. Cl.$^3$ ............................................. C07C 51/58
[52] U.S. Cl. ........................ 260/544 F; 204/158 HA; 260/346.22
[58] Field of Search ............. 260/544 F; 204/158 HA

[56] References Cited

U.S. PATENT DOCUMENTS 2,181,554 11/1939 Kracker et al. ................. 260/544 F
2,289,886 7/1942 Schmerling ......................... 568/716

FOREIGN PATENT DOCUMENTS 707955 7/1941 Fed. Rep. of Germany .
480105 2/1938 United Kingdom .

OTHER PUBLICATIONS

Yagupol'skii, L. M. et al. *Chemical Abstracts,* vol. 55 (1961) #19888h.
Ott, Erwin *Berichte,* vol. 55B (1922) pp. 2108–2125.
Davies, William et al., J. Chem. Society vol. 121 (1922) pp. 2202–2214.
Lovelace, A. M. et al., "Aliphatic Fluorine Compounds" (1958) Reinhold, Publ., p. 143.
J. Chem. Soc., vol. 221, pp. 2204–2215, (1922), "Davies and Perkin: The Chlorination and Bromination of the Toluic Acids, etc.".

*Primary Examiner*—Bernard Helfin
*Attorney, Agent, or Firm*—Cushman, Darby & Cushman

[57] ABSTRACT

α,α,α-trifluoro-o-toluic fluoride is produced in good yield and high purity by reacting anhydrous hydrogen fluoride with 1,1,3,3-tetrachloro-1,3-dihydroisobenzofuran or a mixture of α,α,α-trichloro-o-toluic chloride therewith, the mixture being preferably produced by sufficiently photochlorinating o-toluic chloride in mild conditions.

10 Claims, No Drawings

PROCESS FOR PRODUCING α, α, α-TRIFLUORO-O-TOLUIC FLUORIDE

This invention relates to a process for producing α,α,α-trifluoro-o-toluic fluoride.

Chemical Abstract, 55, 19888h (1961) describes that, when 1,1,3,3-tetrachlorophthalan (also called 1,1,3,3-tetrachloro-1,3-dihydroisobenzofuran and hereinafter referred to as compound (III) is heated to react with antimony trifluoride and thereafter treated with 20% hydrochloric acid, 1,1,3,3-tetrafluorophthalan (also called 1,1,3,3-tetrafluoro-1,3-dihydroisobenzofuran, and hereinafter referred to as compound II) is obtained from the organic layer, while α,α,α-trifluoro-o-toluic amide is obtained from the aqueous layer by treatment with dry ammonia. It can be said that this literature suggests from this disclosure that by reaction of compound (III) with antimony trifluoride α,α,α-trifluoro-o-toluic fluoride [hereinafter referred to a compound (I)] will be by-produced incidentally to compound (II), as shown below:

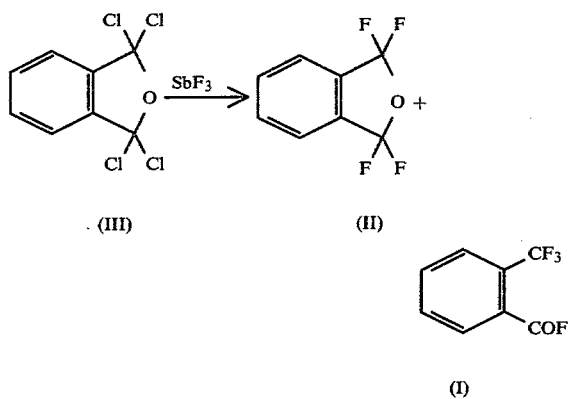

(III)  (II)  (I)

However, it imparts no information of the conditions under which the compound (I) is synthesized in a high yield and a high purity from the compound (III). According to the reproductive experiments by the present inventors, in the case of the above-mentioned reaction it is difficult to recover compounds (II) and (I) respectively from the reaction products by fractional distillation. For this reason it may hardly be said that the process described in said literature is an industrially beneficial process for synthesizing compound (I).

The object of the present invention is to provide a process for obtaining α,α,α-trifluoro-o-toluic fluoride advantageously in industrial scale.

The present inventors have unexpectedly found that compound (I) with high purity can be synthesized by reaction of compound (III) with hydrogen fluoride:

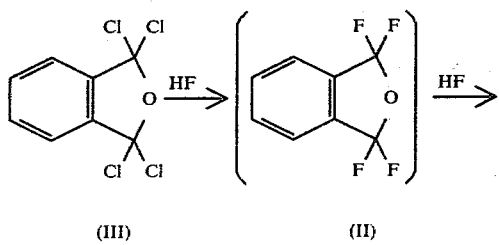

(III)  (II)

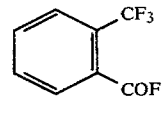

(I)

Thus, according to the present invention there is provided a process for producing α,α,α-trifluoro-o-toluic fluoride, which is characterized by reacting 1,1,3,3-tetrachloro-1,3-dihydroisobenzofuran with hydrogen fluoride.

In the process of this invention, in order to yield compound (I) with high purity it is desirable to enhance opportunities as many as possible for hydrogen fluoride to be brought into contact with compound (II) which is supposed as the intermediate product. That is, with respect to the amount ratio of hydrogen fluoride to compound (III) an excess use of the former is necessary; for example, it is a favorable case to use it in an amount range of about 10 to 20 moles per 1 mole of compound (III). By the reaction from compound (III) to compound (II) in the stoichiometric amount ratio, compound (I) can not be obtained at all. The use of hydrogen fluoride in an excess of about 10 to about 20% of the stoichiometric amount is unfavorable, because it results in a mixture of compounds (II) and (I) and leaves difficulty in the separation and recovery by distillation of the products.

For operating the process of this invention, it is recommended that compound (III) is placed together with anhydrous hydrogen fluoride into a pressure- and corrosion-resistant vessel and they are heated under sealed condition. They may also be reacted under atmospheric pressure in the presence of a suitable fluorination catalyst. When such a catalyst is used, the amount of hydrogen fluoride used may be the stoichiometric amount or a somewhat excess thereover. The heating temperature may be properly selected within the range of about 50° to about 150° C., and particularly the range of about 90° to about 120° C. is preferable.

Meanwhile, the present inventors have otherwise obtained the knowledge that on reaction α,α,α-trichlorotoluic chloride [compound (IV)] with anhydrous hydrogen fluoride compound (II) can be obtained:

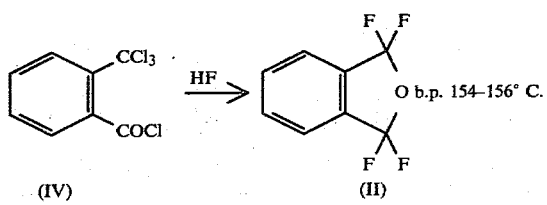

(IV)  (II)

Accordingly, it is deemed that the compounds (III) and (IV) are equivalent in the reaction with anhydrous hydrogen fluoride.

On the other hand, a literature, Chemical Abstracts 17, 383 (1923) teaches that the compound (IV) is obtained in a convention of about 64% from the compound (III) by heating the compound (III) at 220° C. for 0.5 hour.

From the above two informations, another aspect of the invention is to utilize as starting material a mixture of 1,1,3,3-tetrachloro-1,3-dihydroisobenzofuran (compound III) and α,α,α-trichlorotoluic chloride.

Thus, this invention provides also a production process for obtaining compound (I) with high purity by reaction of a mixture of compounds (III) and (IV) with anhydrous hydrogen fluoride. In this invention the reaction of such mixture with anhydrous hydrogen fluoride can be carried out in accordance with the above-mentioned conditions in the case of reaction between compound (III) and anhydrous hydrogen fluoride.

The present inventors have also otherwise found that a mixture of compounds (III) and (IV) can be obtained by sufficient photochlorination of o-toluic chloride (hereinafter referred to as compound VI).

Consequently, this invention further provides a process for synthesizing compound (I) with high purity by sufficient photochlorination of compound (VI) to produce a mixture of compounds (III) and (IV) and by subsequent reaction of the mixture with anhydrous hydrogen fluoride.

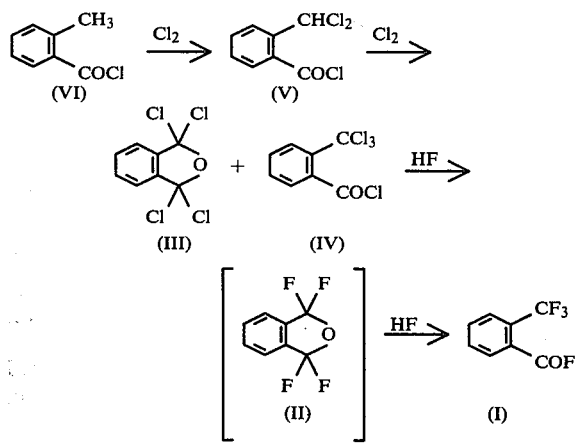

Incidentally, J. Chem. Soc., 121, 2212 (1922) describes that purification of the oily product obtained by chlorination of compound (VI) at 160° to 240° C. for about 10 hours gives not compound (III) but pure compound (IV) having m.p. of 87° C., but this description of said literature is inaccurate because compound (IV) actually is an oily matter (the physical properties are described later).

According to the knowledge of the present inventors, the photochlorination of compound (VI) to compound (V) proceeds with comparative ease, but thereafter, if the conditions are too severe as is the case of the above-mentioned literature, decomposition of compounds (V) and (IV) proceed simultaneously, not only causing troubles such as coloration of the contents into brown but also making it impossible to recover compound (I) with high purity even though the products thus obtained is subjected to the reaction with hydrogen fluoride.

Therefore, in operating the process of this invention it is necessary to carry out the photochlorination under relatively mild conditions, and it is important to control the temperature of the reaction mixture so as not to rise up to the temperature region that promotes the decomposition. The reaction is carried out generally within the temperature range of room temperature to about 140° C.; preferably about 70° to about 130° C.

The photochlorination in this invention can be carried out either in nonsolvent state or in a solvent such as carbon tetrachloride. For the light sources, those usually employed in photochlorination process are acceptable; any of light sources can be used including ultraviolet and tungsten lamps, solar beams, etc.

Further, provided that compound (VI) is photochlorinated under relatively mild conditions sufficiently until compound (V) becomes undetected by an appropriate inspection means, for example, such as gas chromatography and nuclear magnetic resonance spectroscopy, a mixture of compounds (III) and (IV) can be obtained in a good yield. The mixture thus obtained contains compounds (III) and (IV) ordinarily in a weight ratio of about 6:4. Since compound (III) is a white crystalline material with a melting point of 85°–86° C. and compound (IV) is an oily material with a boiling point of 120°–123° C./0.55 mmHg, continuous introduction of the mixture for reaction with anhydrous hydrogen fluoride is preferably carried out under such conditions as compound (III) exists in a liquid state.

The mixture thus obtained can be subjected to the next reaction with anhydrous hydrogen fluoride after remaining dissolved chlorine has been purged away in ordinary way. The reaction of this mixture with hydrogen fluoride may be carried out in accordance with the conditions mentioned above.

After the reaction with anhydrous hydrogen fluoride has been completed, compound (I) is extracted from the resultant mixture with a suitable extraction solvent, washed with water, dried, thereafter the solvent is removed, and distilled under atmospheric pressure, whereby compound (I) is obtained as a liquid with a boiling point of 160°–162° C. in a yield of 70% or more based on compound (III) or the mixture of compounds (III) and (IV).

As described above, according to the process of this invention compound (I) can be synthesized in a good yield by reacting the mixture of compounds (III) and (IV) which are the reaction products of photochlorination of compound (VI), directly as it is with anhydrous hydrogen fluoride. Hence, this process is exceedingly valuable as an industrial scale process for producing compound (I) which is a useful material for producing various useful compounds such as o-trifluoromethyl-m'-isopropoxybenzoyl anilide disclosed in West German Pat. No. 2731522.

The present invention is explained by way of Examples.

EXAMPLE 1

Compound (VI)→Compound (III)+Compound (IV)→Compound (I)

A reaction was carried out by passing dry chlorine into 43 g (0.27 mole) of o-toluic chloride at 110°–120° C. under irradiation with an ultraviolet lamp. The reaction mass was occasionally withdrawn in an amount necessary for gas chromatographic analysis to examine the change of the peak of α,α-dichloro-o-toluic chloride by comparing with an authentic sample, and the introduction of chlorine was stopped after the peak disappeared. When part of the reaction mass was analyzed as it is by gas chromatography it was possible to make sure that 1,1,3,3-tetrachloro-1,3-dihydroisobenzofuran and α,α,α-trichloro-o-toluic chloride were formed in a mixed ratio by weight of about 6:4, yield 67 g (chlorination yield 93.4%).

After remaining dissolved gaseous chlorine was purged off by introducing gaseous nitrogen into the mixture obtained, 7.6 g (0.029 mole) of the resulting mixture was placed into a Hastelloy autoclave, 8.5 g (0.425 mole) of anhydrous hydrogen fluoride was added, and the mixture was heated and stirred at 110°–125° C. under sealed condition. Gaseous hydrogen chloride evolved with proceeding of the reaction was drawn out. After 4 hour's reaction, the reaction mass was left to cool down to room temperature, the autoclave was cooled with ice-cold water, and it was opened. After a small amount of sodium fluoride was added, the reaction mixture was poured with the aid of methylene dichloride into a polyethylene flask which had been loaded with ice and sodium hydrogen carbonate. The reaction product was subjected to extraction with methylene dichloride, thoroughly washed with water, dried over anhydrous magnesium sulfate, and thereafter methylene dichloride was distilled off under atmospheric pressure. On distillation of the residue under atmospheric pressure, 4.5 g of α,α,α-trifluoro-o-toluic fluoride was obtained as a liquid with a boiling point of 160°–162° C. The yield from the mixture was 80%.

EXAMPLE 2

Compound (VI)→Compound (III)+Compound (IV)

Five g (0.032 mole) of o-toluic chloride was dissolved in 150 ml of carbon tetrachloride and reaction was carried by passing dry chlorine into the solution under irradiation with an ultraviolet lamp while refluxing carbon tetrachloride. From the reaction mass an amount thereof necessary for gas chromatographic analysis was occasionally withdrawn to examine the change of the peak of α,α-dichloro-o-toluic chloride by comparing with an authentic sample, the introduction of chlorine was stopped after the peak was disappeared. Part of the oily matter obtained by reduced pressure distillation for removal of carbon tetrachloride was withdrawn, and on analyzing it by gas chromatography it was possible to ascertain that 1,1,3,3-tetrachloro-1,3-dihydroisobenzofuran and α,α,α-trichloro-o-toluic chloride was formed in a mixed ratio by weight of about 6:4, yield 6.6 g (chlorination yield 80%).

This mixture could be reacted with anhydrous hydrogen fluoride in accordance with the reaction with anhydrous hydrogen fluoride described in Example 1.

That is, when this mixture was reacted with anhydrous hydrogen fluoride in accordance with the reaction with anhydrous hydrogen fluoride as described in Example 1, α,α,α-trifluoro-o-toluic fluoride was obtained in a yield of 75% (based on the mixture), b.p. 160°–162° C.

Further, for reference, the mixture obtained as mentioned above was left to cool down to room temperature and the precipitated white crystals were filtered off and recrystallized in hexane, whereby 1,1,3,3-tetrachloro-1,3-dihydroisobenzofuran with melting point of 85°–86° C. was obtained in high purity, 'H-NMR (CDCl$_3$): 7.72 (S) (internal standard trimethylsilane).

By repeated reduced pressure distillation of the filtrate α,α,α-trichloro-o-toluic chloride, a colorless, clear, oily matter, is obtained in high purity, b.p. 120°–123° C./0.5 mmHg.

EXAMPLE 3

Compound (III)→Compound (I)

Into a hastelloy autoclave 9.8 g (0.038 mole) of 1,1,3,3-tetrachloro-1,3-dihydroisobenzofuran was placed, 10 g (0.5 mole) of anhydrous hydrogen fluoride was added, and the mixture was heated and stirred at 110°–125° C. Gaseous hydrogen chloride evolved with proceeding of the reaction was drawn off. After 4 hour's reaction, the reaction mass was left to cool down to room temperature, and the autoclave was cooled with ice-cold water and opened. A small amount of sodium fluoride was added, and thereafter, the mixture was introduced with the stream of methylene dichloride into a polyethylene flask which had been loaded with ice and sodium hydrogen carbonate. The reaction product was subjected to extraction with methylene dichloride, thoroughly washed with water, dried over anhydrous magnesium sulfate, and thereafter, methylene dichloride is distilled off under atmospheric pressure. Atmospheric pressure distillation of the residue gave 5.2 g of colorless, clear liquid. On analizing a part of the liquid by gas chromatography, no 1,1,3,3-tetrafluoro-1,3-dihydroisobenzofuran was detected and there exists only the object product, α,α,α-trifluoro-o-toluic fluoride, b.p. 160°–162° C., yield 71%.

REFERENCIAL EXAMPLE 1

Forty g of α,α,α-trichloro-o-toluic chloride was heated to 110°–130° C. and stirred for 7 hours under irradiation with an ultraviolet lamp. Next, dry hydrogen chloride was passed at the same temperature for 4 hours, and subsequently dry gaseous chlorine was passed also at the same temperature for 4 hours. The reaction mass was left to cool down to room temperature, analyzed by both gas chromatography and nuclear magnetic resonance spectrography, and the results showed no change at all, recovered amount 39.2 g, percentage recovery 98%.

REFERENCIAL EXAMPLE 2

Ten g of 1,1,3,3-tetrafluoro-1,3-dihydroisobenzofuran was placed into a Hastelloy autoclave, stirred and heated for 5 hours with an oil bath at 120°–150° C., and then post-treated in accordance with the post-treatment method described in Example 1, whereby 9.5 g of 1.1,3,3-tetrafluoro-1,3-dihydroisobenzofuran was recovered. Additionally, it was ascertained by both gas chromatographic and nuclear magnetic resonance spectrographic analyses that no α,α,α-trifluoro-o-toluic fluoride was formed.

This shows that 1,1,3,3-tetrafluoro-1,3-dihydroisobenzofuran, when heated, does not change into α,α,α-trifluoro-o-toluic fluoride.

REFERENCIAL EXAMPLE 3

A mixture was prepared by mixing 30.2 g (0.2 mole) of m-isopropoxyaniline with 31.8 g (0.3 mole) of sodium carbonate in 150 ml of water. While stirring the mixture α,α,α-trifluoro-o-toluic fluoride was added dropwise thereto. After the addition, the mixture was stirred at 30° to 35° C. for 30 minutes and then at 65° to 70° C. for 45 minutes, cooled down to room temperature. The precipitated crystals formed were taken off by filtration, washed with diluted hydrochloric acid solution, washed with water, and dried in air to obtain white crystals with m.p. of 108° C. in a yield of 92.7%.

We claim:

1. A process for producing α,α,α-trifluoro-o-toluic fluoride, which is characterized by reacting 1,1,3,3-tetrachloro-1,3-dihydroisobenzofuran or a mixture of 1,1,3,3-tetrachloro-1,3-dihydroisobenzofuran with α,α,α-trichloro-o-toluic chloride, with hydrogen fluoride.

2. The process according to claim 1, wherein the reaction is carried out in a mole ratio of 10 to 20 moles of hydrogen fluoride to 1 mole of 1,1,3,3-tetrachloro-1,3-dihydroisobenzofuran or the mixture.

3. The process according to claim 1, wherein the reaction is carried out at a temperature of 50° to 150° C.

4. The process according to claim 1, wherein the mixture consists of 6 parts by weight of 1,1,3,3-tetrachloro-1,3-dihydroisobenzofuran and 4 parts of α,α,α-trichloro-o-toluic chloride.

5. The process according to claim 1 or 4, wherein the mixture is produced by sufficiently photochlorinating o-toluic chloride at a temperature of 70° C. to 140° C.

6. The process of claim 2 wherein the temperature is 50° to 150° C.

7. The process of claim 6 wherein there is employed a mixture of 1,1,3,3-tetrachloro-1,3-dihydroisobenzofuran with α,α,α-trichloro-o-toluic chloride.

8. The process of claim 3 wherein there is employed a mixture of 1,1,3,3-tetrachloro-1,3-dihydroisobenzofuran with α,α,α-trichloro-o-toluic chloride.

9. The process of claim 2 wherein there is employed a mixture of 1,1,3,3-tetrachloro-1,3-dihydroisobenzofuran with α,α,α-trichloro-o-toluic chloride.

10. The process of claim 1 wherein there is employed a mixture of 1,1,3,3-tetrachloro-1,3-dihydroisobenzofuran with α,α,α-tetrachloro-o-toluic chloride.

* * * * *